(12) United States Patent
Antonucci et al.

(10) Patent No.: US 10,190,972 B2
(45) Date of Patent: Jan. 29, 2019

(54) DEVICE FOR MANAGING PULSES IN PUMP-PROBE SPECTROSCOPY

(75) Inventors: Laura Antonucci, Orsay (FR); Adeline Bonvalet, Orsay (FR); Manuel Joffre, Palaiseau (FR); Xavier Solinas, Palaiseau (FR)

(73) Assignees: ECOLE POLYTECHNIQUE, Palaiseau (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 343 days.

(21) Appl. No.: 14/122,005

(22) PCT Filed: Jun. 28, 2012

(86) PCT No.: PCT/FR2012/051494
§ 371 (c)(1),
(2), (4) Date: Jun. 17, 2014

(87) PCT Pub. No.: WO2013/001242
PCT Pub. Date: Jan. 3, 2013

(65) Prior Publication Data
US 2014/0293288 A1    Oct. 2, 2014

(30) Foreign Application Priority Data
Jun. 29, 2011    (FR) ..................................... 11 55799

(51) Int. Cl.
| | | |
|---|---|---|
| *G01N 21/25* | (2006.01) | |
| *G01N 21/17* | (2006.01) | |
| *G01N 21/63* | (2006.01) | |
| *G01B 9/02* | (2006.01) | |

(52) U.S. Cl.
CPC ....... *G01N 21/255* (2013.01); *G01B 9/02001* (2013.01); *G01N 21/17* (2013.01);
(Continued)

(58) Field of Classification Search
CPC .... G01N 21/255; G01N 21/17; G01N 21/636; G01N 2021/1736; G01N 2021/1791; G01N 2021/1789
See application file for complete search history.

(56) References Cited

U.S. PATENT DOCUMENTS

| | | |
|---|---|---|
| 5,258,612 A | 11/1993 | Clark et al. |
| 6,552,799 B1 | 4/2003 | Wright et al. |
| | | (Continued) |

FOREIGN PATENT DOCUMENTS

WO    2007045773    4/2007

OTHER PUBLICATIONS

International Search Report for corresponding application PCT/FR2012/051494 filed Jun. 28, 2012: dated Aug. 20, 2012.
(Continued)

*Primary Examiner* — Hwa Andrew Lee
(74) *Attorney, Agent, or Firm* — Cantor Colburn LLP (57) ABSTRACT

A device for managing light pulses for measuring the reaction of a sample exposed to a first light pulse, the measurement being performed by analysis of a signal emitted by the sample subjected to a second light pulse, shifted with respect to the first pulse by a determined interval of time, the device including two optical detectors for detecting the pulses of two light beams emitted by two pulsed laser sources, respectively, each beam emitting pulses with respective repetition frequencies that are different, arbitrary and stable over a determined period in the direction of the sample; the detectors being connected to a computer for determining the interval of time between two pulses coming from the first and the second beam, respectively, and constituting the first and second pulses; the computer being connected to an analyzer for measuring the reaction of the sample having as input parameter the interval of time between the two pulses, (Continued)

where the computer uses an algorithm making use of the stability of the repetition frequencies for determining the interval of time.

10 Claims, 5 Drawing Sheets

(52) U.S. Cl.
CPC ... *G01N 21/636* (2013.01); *G01N 2021/1736* (2013.01); *G01N 2021/1789* (2013.01); *G01N 2021/1791* (2013.01)

(56) References Cited

U.S. PATENT DOCUMENTS

2006/0191884 A1    8/2006    Johnson et al.
2008/0186486 A1    8/2008    Gusev

OTHER PUBLICATIONS

Fritz Keilmann, "Time-domain mid-infrared frequency-comb spectrometer", Optics Letters / vol. 29, No. 13 / Jul. 1, 2004, pp. 1542-1544.
Jens Bredenbeck, "Continuous scanning from picoseconds to microseconds in time resolved linear and nonlinear spectroscopy", Review of Scientific Instruments, vol. 75, No. 11, Nov. 2004, pp. 4462-4466.
Y. Takagia, "Subpicosecond optical sampling spectrometer using asynchronous tunable mode-locked lasers", Review of Scientific Instruments, vol. 70, No. 5, May 1999, pp. 2218-2224.
A. Bartels, "Femtosecond time-resolved optical pump-probe spectroscopy at kilohertz-scan-rates over nanosecond-time-delays without delay line", Applied Physics Letters 88, 041117 (2006).

DEVICE FOR MANAGING PULSES IN PUMP-PROBE SPECTROSCOPY

TECHNICAL FIELD

The present invention relates to a device for managing light pulses for measuring the reaction of a sample exposed to a first light pulse called the "pump" pulse, the measurement being performed by analysis of a light signal emitted by the sample subjected to a second light pulse, called the "probe" pulse, shifted with respect to the "pump" pulse by a determined interval of time.

BACKGROUND

The field benefiting from this invention is that of pump-probe spectroscopy and, in a general manner, any application that requires the use of two ultra-short laser pulses separated by a known and variable time delay making it possible to scan the total time interval to be investigated.

In recent years, studies on the dynamics of biological systems have been the subject of a good deal of research. It has notably been demonstrated that such dynamics can, in certain cases, exhibit continuous evolution over several orders of time, ranging from the picosecond to the second.

Pump-probe spectroscopy is a technique that makes it possible to measure the temporal dynamics of a system during a reaction: a pump pulse triggers a reaction, then a time-shifted probe pulse measures the changes caused. It is then necessary to be able to shift one laser pulse with respect to another over the whole time range studied, with the requirement that this shift be precise to the nearest picosecond.

Currently, three means exist for generating two pulses separated by a known and variable delay.

The first means consists in using a single laser system, the beam of which is separated into two branches. One of the branches is delayed with respect to the other using a mechanical delay line. This system is limited to the picosecond-nanosecond range by the length of the delay line. Moreover, special care is required to retain adequate pointing stability during the mechanical scan.

The second means consists in using two unsynchronized laser oscillators. The delay is chosen by selecting for the amplification the pulse pair with the delay closest to the desired delay. The selection is generally performed by the opening-closing of a Pockels cell around the desired pulse. Because of the asynchronism between the two laser oscillators and the resulting jitter over time, the real delay between the two pulses thus selected is known with a precision that cannot fall below the oscillation period of the laser cavities, i.e. typically in the order of ten or so nanoseconds. In compensation, this system makes it possible to produce arbitrarily long delays.

The third means consists in using two synchronized laser oscillators, the delay of which is made to vary by varying their relative time phase. Associated with a pre-amplification selection as described in the context of the second means, this system overcomes the limitations of the previous solutions by allowing the production of long delays while retaining a precision in the order of picoseconds. However, it demands a costly and complex implementation which cannot be performed a posteriori on standard commercial laser oscillators, unless the manufacturer has made provision for this functionality right from the design of the laser. This system is therefore not accessible to most potential users. Analogously, it is possible to use laser oscillators of different frequencies by making use of the principle of stroboscopy applied to the femtosecond domain, the time coincidence between the two pulse trains being measured by an optoelectronic device. However, to work well in the proposed implementations, this approach demands that the frequencies of the two oscillators be neighboring and known with a very high degree of precision, which requires active control of the laser cavity lengths. This is generally not the case if this was not planned before the acquisition of the systems.

These various methods have been described in various publications, of which the most important are:

Bredenbeck, Helbing and Hamm., Rev. Sci. Instrum. Vol. 75 p. 4462. This article from 2004 describes a synchronous electronic scanning solution proposed by the Institut de Chimie-Physique in Zurich. Long delays are given in multiples of the repetition period of the oscillators through the selection, by a Pockels cell, of the pulse to be amplified. Short delays are generated by introducing a known phase between the two laser oscillators. With this method it is possible to attain a precision of 2 ps over an interval of up to 50 µs.

In 1999 Takagi and Adachi (RSI Vol. 70, p. 2218) introduced the method of asynchronous optical scanning. The scanning is obtained by introducing a known repetition rate difference between the two oscillators. If the introduced difference is negligible with respect to the repetition frequency $f_1$ and $f_2$ of the two oscillators, it has been demonstrated that this creates a magnification for the time axis $f_1/f_2$ and consequently an increment for the spectral resolution. In Takagi's study, a temporal magnification of 760000 times was measured.

In 2004 (Keimann, Goble and Holzwarth, "Time domain mid-infrared frequency-comb spectrometer", Opt. Lett. 29, p. 1542 (2004)), this advantage was improved to ultimately obtain a temporal magnification of 45500000 times, which corresponds to 13 $cm^{-1}$ of spectral resolution. These studies were conducted with femtosecond lasers, emphasizing the discrete nature of pulse spectra, which cleared the way for "frequency comb spectroscopy", which makes use of the phenomenon of beating between each frequency line forming the spectrum of the two shifted pulses. The advantages with respect to conventional Fourier transform spectroscopy experiments lie in the sensitivity of measurement, the spectral width and the spectral resolution obtained with measurement times of a few tens of microseconds.

A method of optoelectronic synchronization has also been proposed in patent application WO/2007/045773 but the temporal resolution obtained is only beneficial when the frequencies of the two oscillators are neighboring.

It would therefore be advantageous to obtain a device for managing the laser pulses making it possible to obtain a delay between two pulses that can vary from the picosecond to the second with picosecond precision, and this while using standard femtosecond lasers.

BRIEF SUMMARY

To resolve one or more of the aforementioned drawbacks, a device for managing light pulses for measuring the reaction of a sample exposed to a first light pulse called the "pump" pulse, the measurement being performed by analysis of a light signal emitted by the sample subjected to a second light pulse, called the "probe" pulse, shifted with respect to the "pump" pulse by a determined interval of time, comprises:

two optical detectors suited to detecting the pulses of two light beams emitted by two pulsed laser sources, respectively, the first beam being called the "pump" beam and the second beam being called the "probe" beam, each beam emitting pulses with respective repetition frequencies that are different, arbitrary and stable over a determined period in the direction of said sample; the detectors being connected to a computer suited to determining the interval of time between two pulses coming from the first and the second beam, respectively, and constituting the "pump" and "probe" pulses for measuring the reaction of the sample; said computer comprising a connector to an analyzer for measuring the reaction of the sample, having as input parameter the interval of time determined by the first computer for the measurement involving the two pulses.

Moreover, the computer uses an algorithm making use of the stability of the repetition frequencies for determining the interval of time.

This device thus makes it possible, advantageously, to presuppose free operation of the two oscillators, this operation not requiring any control and feedback system for the optical cavities. Furthermore, the temporal precision is not directly proportional to the frequency difference between the two oscillators and can thus be easily less than a picosecond for the typical frequencies used in standard lasers. Thus, most of the time, it is simple to implement the device in an experiment using two pre-existing amplified laser systems, just by sending a small fraction of the oscillator beams to the device.

Particular features or embodiments, which may be used alone or in combination, include:

- the device furthermore comprises two pulse selectors positioned on each of the two beams, respectively, each selector being suited to transmitting toward a sample a particular pulse of the beam on which it is positioned, the transmitted pulse being selected by the computer in such a way that the interval of time between the selected pulse of the first beam and the selected pulse of the second beam is a predetermined value;
- the pulse selectors are light amplifiers;
- the computer is suited to detecting time coincidences between a pulse of the first beam and a pulse of the second beam, and to counting the number of pulses produced by each beam between two coincidences in order to determine the law of evolution for the interval of time between two pulses by interpolation or extrapolation;
- the computer is suited to selecting a series of pulse pairs, each pair being composed of a pulse of the first beam and of a pulse of the second beam, in such a way that all of the time intervals for the series of pulse pairs allows sampling of a predetermined measurement interval;
- the optical detectors are combined in the form of an interferometer, the interference signal of which is detected by at least one photodiode in such a way that the temporal superposition of two pulses triggers a coincidence signal for the computer; and/or
- the optical detectors each have one photodiode suited to transforming each pulse into an electrical signal acting as input signal for an electronic "time-to-digital converter" (TDC) circuit.

BRIEF DESCRIPTION OF THE DRAWINGS

The invention will be better understood on reading the following description, made only by way of example, and with reference to the appended figures, in which.

DETAILED DESCRIPTION

Figure 1:
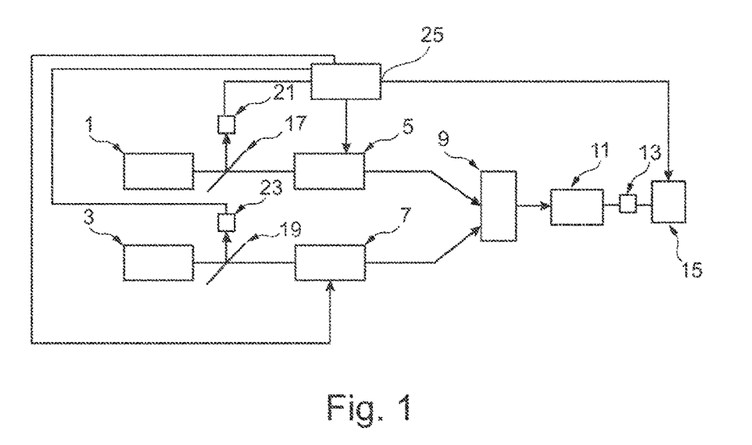
FIG. 1 is a schematic view of a pump-probe spectroscopy system having a device according to a first embodiment of the invention.

With reference to FIG. 1, a device operating on the principle of heterodyne sampling conventionally comprises a "pump" pulsed laser source 1 and a "probe" pulsed laser source 3 emitting a "pump" beam and a "probe" beam, respectively. The two laser sources are typically femtosecond lasers, thus emitting pulses in the order of one hundred or so femtoseconds. The "pump" and "probe" pulse durations are equal or unequal. Similarly, the central wavelengths of the "pump" and "probe" beams are equal or unequal depending on the measurement to be performed.

Each beam passes through an optical amplifier 5, 7 before being combined by a combiner 9. For example, the combiner 9 comprises a mirror and a semi-transparent plate.

The beams thus combined are then directed toward an experimental device 11 in which a sample for measurement is placed.

The response of the sample is received by a photodetector 13 then transmitted to an acquisition system 15.

In the embodiment of the device for managing light pulses in FIG. 1, a sample slide 17, 19 is installed on the path of each beam at the output of each laser source 1, 3 so as to pick up a trace of each pulse on photodetectors 21, 23. Those skilled in the art will understand that the transparency of the slides is chosen so as to send to the photodetectors 21, 23 only the power necessary to their operation.

The photodetectors 21, 23 are connected to a computer 25.

The computer 25 comprises a control interface for the optical amplifiers 5, 7 and is connected to the acquisition system 15.

The operation of the device is as follows.

In general, two oscillators designed for free operation produce two combs of pulses 31, 33 of different and highly stable frequencies. The relative delay, or relative time phase, between the two combs progressively travels between the moment when a coincidence occurs and the following coincidence according to the principle of asynchronous scanning, FIGS. 2.

Figure 2:
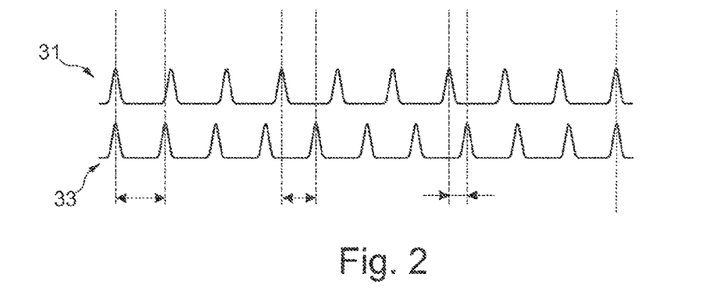
FIG. 2 is a timing diagram for the pulses of two lasers having different repetition frequencies according to the principle of asynchronous scanning, and showing the coincidences.

$\Omega_1$ and $\Omega_2$ being the respective frequencies of the lasers, it is possible to define a time phase for each of the lasers: $\Phi_1=\Omega_1(t-\tau_1)$ and $\Phi_2=\Omega_2(t-\tau_2)$ ($\tau_1$ and $\tau_2$ defining the time shift of the two pulse trains and t being the time coordinate). These laws being known, it is then possible to foresee with precision the relative phase $\Delta\Phi=\Phi_2-\Phi_1$, and therefore the delay between all the pulses produced by the two oscillators.

To measure the phase laws of the two oscillators, the computer detects the coinciding pulses while precisely counting the number of pulses produced by each of the two lasers between the coincidences. This evolution law for the interval of time between two pulses is therefore determined by interpolation or extrapolation. This makes it possible to determine $\Omega_2/\Omega_1$, in particular, with very high precision.

Indeed, let $\Delta t$ be the interval of time during which it may be supposed that the oscillators remain perfectly stable, that is to say that there is no measurable jitter phenomenon. With current oscillators, $\Delta t$ is typically in the order of 1 ms. T is the period of the pulse train and is equal to around 10 ns for 100 MHz oscillators, and $\delta\tau$ is the temporal precision of the coincidence measurement.

The number of pulses produced during the period $\Delta t$ has a value of $N=\Delta t/T$, which therefore corresponds to a number of coincidences in the order of $n=N\delta\tau/T$. Taking into account the stability of the oscillators, the precision over the measurement of the parameters $\tau_1$ and $\tau_2$ is therefore in the order of $\delta\tau/\sqrt{n}$. The ultimate precision of the device is therefore linked to the method used for detecting the coincidences.

Figure 3:
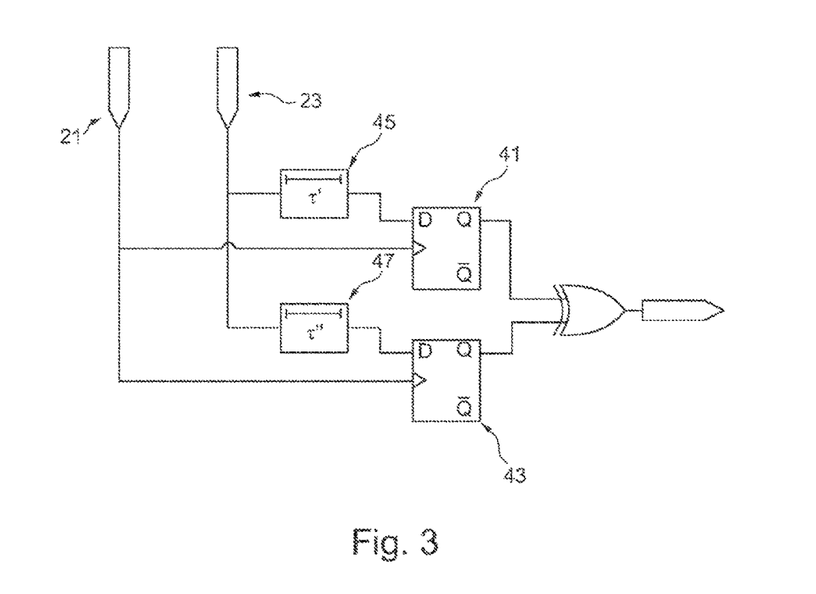
FIG. 3 is a schematic view of an electronic assembly for an acquisition card of the device in FIG. 1.

In the embodiment in FIG. 3, the detection of the coincidences is totally electronic.

The photodetectors 21, 23 are fast photodiodes, the electrical signal from which is sent to an electronic card of the computer 25.

The electrical signals are sent to two flip-flops D 41, 43. One of the signals is used as a common clock, and the other signal is distributed successively to the input of the first flip-flop and then of the second flip-flop with a slight delay, $\tau'$ for a first delay line 45 and $\tau''$ for a second delay line 47. At each new clock pulse, a coincidence is signified by a state difference between the outputs of the flip-flops.

Figure 4A:
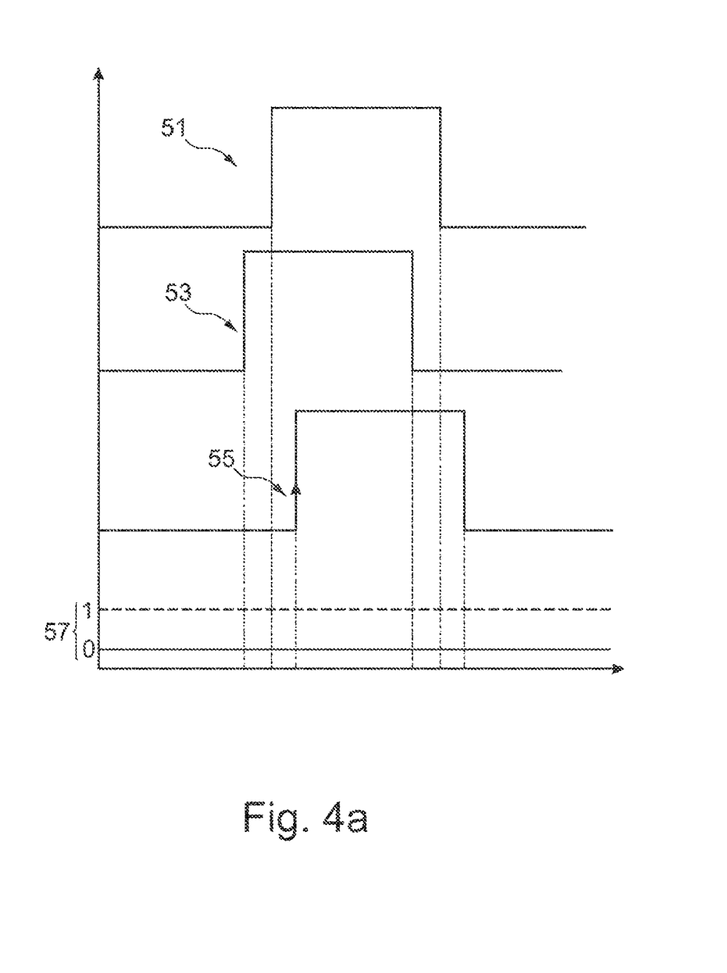
FIG. 4A is a timing diagram for the electronics in FIG. 3 showing a coincidence signal in a phase where the two lasers are not in coincidence.
Figure 4B:
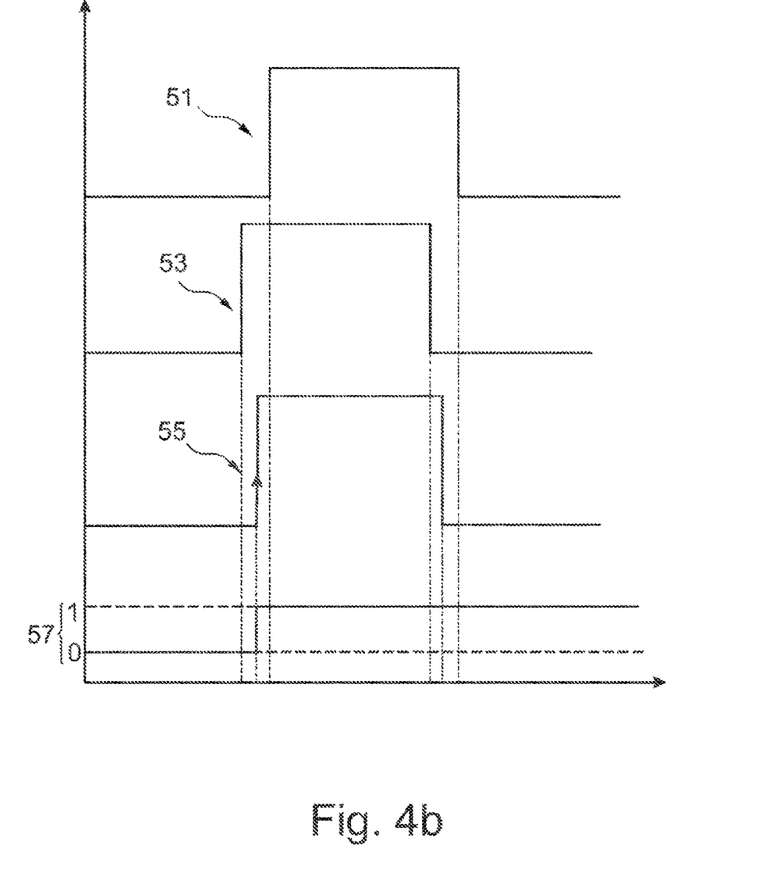
FIG. 4B is a timing diagram for the electronics in FIG. 3 showing a coincidence signal in a phase where the two lasers are in coincidence.

FIGS. 4A and 4B show the timing diagram for the signals 51, 53 at the output of the delay lines 45, 47 and for the signal 55 at the output of the photodetector and acting as clock for the two flip-flops D 41, 43. The signal 57 shows the signal at the output of the combinational exclusive OR for the two outputs of the flip-flops D. FIG. 4A shows the signals when the two lasers are not in coincidence, and the signal 57 therefore remains at 0, and FIG. 4B shows the signals when a coincidence occurs, the signal 57 then flipping from 0 to 1.

The inventors have produced a prototype according to this outline which allows a precision in the order of $\delta\tau\approx 30$ ps. Two optical fibers coupled to two Si PIN photodiodes have been connected by differential pairs to the coincidence detector and to the computer embedded in an FPGA of the Spartan family from the manufacturer Xilinx. With the numerical values above, this gives a rate of 300 coincidences per millisecond. Laser frequencies that are sufficiently stable with respect to this rate allow these coincidences to be averaged to obtain a final precision of slightly less than 2 ps. This value can be further improved by using a specialized circuit (ASIC) or by increasing the coincidence rate by reducing the number of electronic paths with different and known delays.

As a variant, it will be noted that it is also possible to use known devices of the time-to-digital converter type.

This makes it possible to make use of pulse pairs even when there is no coincidence and therefore to increase the number n of acquisitions contributing to the measurement and thus to improve the precision of the latter.

Figure 5:
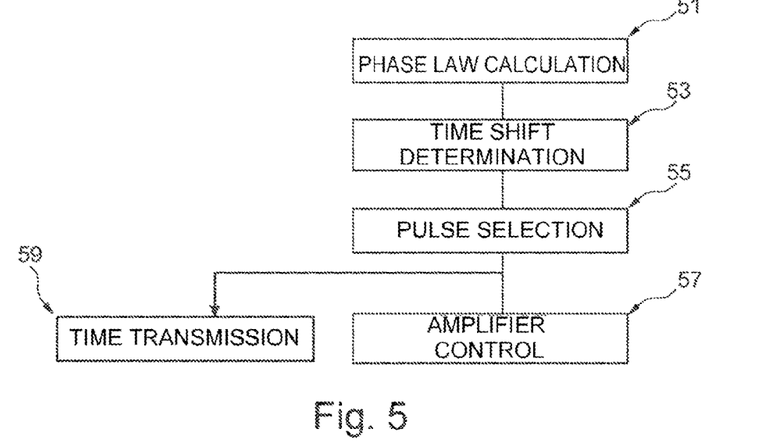
FIG. 5 is a flowchart for the operation of the device in FIG. 1.

Thus, in FIG. 5, having taken, in step 51, a precise measurement of the phase laws of the two oscillators, the computer is then capable of determining, in step 53, the value of the time shift between any pulse of the "pump" signal and any subsequent pulse of the "probe" signal. And therefore, for a determined shift value, it is capable of selecting, in step 55, a pair of "pump"-"probe" pulses having this value of time shift.

The computer 25 then controls, in step 57, the amplifiers 5, 7 to let through, and amplify only, the corresponding pulses. In parallel, in step 59, it informs the acquisition system 15 of the time between the "pump" pulse and the "probe" pulse.

As indicated in the introduction, in "pump"-"probe" spectroscopy, the aim is to measure the reaction of a sample over a varied range of times separating the "pump" pulse from the "probe" pulse so as to study the dynamics of the sample.

Owing to the device described, it is enough to preliminarily configure the range of times to be studied, for example from 1 ns to 1 ms, and the number of samples, for example with a step of 1 ps, and the computer is then capable of selecting the series of pulses covering the requested range. It will be noted that the measurements can be in any order and can depend only on the sequence of the pulses in such a way as to minimize the measurement time. Therefore, the computer 25 is linked to the acquisition system 15 so as to supply the latter with information about the time between pulses corresponding to the measurement in progress. Simple sorting processing over the duration of the times then makes it possible to order the measurements. A beneficial variant comprises not using the selectors 5 and 7, which makes it possible to make use of all the pulse pairs produced by the two oscillators 1 and 3, the delays being determined a posteriori by the computer. In this case, the temporal dynamics are limited to the period of the oscillators, typically in the order of 10 ns.

Figure 6:
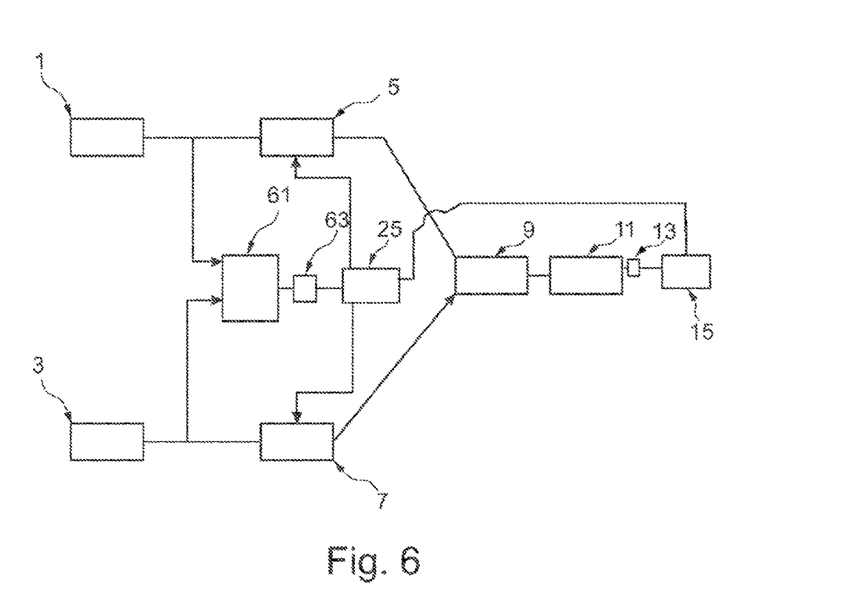
FIG. 6 is a schematic view of a pump-probe spectroscopy system having a device according to a second embodiment of the invention.

In a second embodiment, FIG. 6, the photodetectors 21, 23 and the electronic acquisition card are replaced by an optical device.

The latter comprises an interferometer 61, possibly a fiber interferometer, on which the two laser beams are aligned. The coincidences corresponding to the temporal superposition of two pulses are detected by the optical linear interference generated. The interference signal is detected with a photodiode 63 and sent to an acquisition card in the computer 25, which compares it with a threshold value. As a variant, it is possible to use a photodiode on each of the two outputs of the interferometer to carry out differential detection.

Optical detection of coincidences as described makes it possible to have a precision $\delta\tau$ in the order of the duration of the pulses, i.e. typically 100 fs. With the numerical values above, this gives a coincidence rate $n/\Delta t$ in the order of one coincidence per millisecond. It is possible to increase the coincidence rate to the detriment of temporal precision by placing a filter reducing the spectral range in front of the photodetector. Such a filter is also necessary when the spectra of the two oscillators are not identical. Finally, in the case where the spectral overlap between the two oscillators is nil, the coincidences can be detected using a non-linear optical process (two-photon absorption, frequency sum etc.).

The invention has been illustrated and described in detail in the drawings and in the previous description. The latter must be considered as illustrative and given by way of example, rather than as limiting the invention to this single description. Many variant embodiments are possible.

In the claims, the word "comprising" does not exclude other elements and the indefinite article "a/an" does not exclude a plurality.

The invention claimed is:

1. A device for managing light pulses for measuring a reaction of a sample exposed to a first light pulse called a "pump" pulse, the measurement being performed by analysis of a signal emitted by the sample subjected to a second light pulse, called a "probe" pulse, temporally shifted with respect to the "pump" pulse by a determined time interval, the device comprising:
   two ultrashort pulsed oscillators of different pulse frequencies, stable over a determined period Δt, said oscillators being characterized by their relative phase which allows to foresee the delay between all the pulses produced by the two oscillators,
   two optical detectors beamed to detecting the pulses of two light beams emitted by two ultrashort pulsed oscillators respectively, the first beam being called the "pump" beam and the second beam being called the "probe" beam, in the direction of said sample; the detectors being connected to
   a computer configured to accumulate during said determined period Δt measurements of the relative phase and determine, based on these measurements, the value of the time delays between subsequent pump and probe pulses, with a precision improving with the square root of the number of measurements, hence in the picosecond or sub-picosecond domain,
   an acquisition system connected to the computer and configured to receive from the computer the time delay values and to acquire signals emitted by the sample in order to analyze its reaction to the pairs of pulses for determined values of time delay.

2. The device as claimed in claim 1, comprising two pulse selectors positioned on each of the two beams, respectively, each selector being configured to transmit toward a sample a particular pulse of the beam on which it is positioned.

3. The device as claimed in claim 2, wherein the pulse selectors are light amplifiers.

4. The device as claimed in claim 3, wherein the amplifiers are configured to amplify the pairs of pump-probe pulses having the predetermined value.

5. A method for measuring a reaction of a sample exposed to a first light pulse called a pump pulse, the measurement being performed by analysis of a signal emitted by the sample subjected to a second light pulse, called a probe pulse, temporally shifted with respect to the pump pulse by a determined time interval, both light pulses being emitted by ultrashort pulsed oscillators having different repetition frequencies that are arbitrary and stable over a determined period Δt, the method comprising:
   repeated measurements of the relative phase of the two oscillators during the period Δt;
   the determination, based on these measurements, of the value of the time delays between subsequent pump and probe pulses, with a precision improving with the square root of the number of measurements, hence in the picosecond or sub-picosecond domain; and
   the analysis of the reaction of the sample with an acquisition system for pairs of a pump pulse and a subsequent probe pulse of determined values of time delay.

6. The method as claimed in claim 5, wherein the predetermined value of time interval is transmitted to the acquisition system.

7. The method as claimed in claim 5, comprising selecting at least one pair of pump and probe pulses having a determined value of time interval.

8. The method as claimed in claim 5, comprising controlling, during the selection selectors to let through and amplify only said at least one pair having the predetermined value of time interval.

9. The device as claimed in claim 1, wherein the optical detectors are fast photodiodes, the electrical signal from which is sent to an electronic card of the computer configured to detect coincidences between pairs of a pulse of the first beam and a pulse of the second beam with a temporal precision δτ limited by the electronics, resulting in an accuracy in the order of δτ divided by the square root of n, where n is the number of measurements performed during the stability period Δt of the two oscillators.

10. The method as claimed in claim 5, comprising the measurement of the relative phase even when there is no coincidence between a pulse of the first beam and a pulse of the second beam by means of optical detectors each having one photodiode configured to transform each pulse into an electrical signal acting as input signal for an electronic "time-to-digital converter" (TDC) circuit.

* * * * *